(12) United States Patent
Farmer

(10) Patent No.: US 9,470,632 B2
(45) Date of Patent: Oct. 18, 2016

(54) PLASMONIC STRUCTURE WITH ENHANCED BANDWIDTH

(71) Applicant: INTERNATIONAL BUSINESS MACHINES CORPORATION, Armonk, NY (US)

(72) Inventor: Damon B. Farmer, White Plains, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/445,759

(22) Filed: Jul. 29, 2014

(65) Prior Publication Data

US 2016/0033401 A1    Feb. 4, 2016

(51) Int. Cl.
*G01N 21/55* (2014.01)
*G01N 21/552* (2014.01)

(52) U.S. Cl.
CPC .................. *G01N 21/553* (2013.01)

(58) Field of Classification Search
USPC ............................... 356/445–448
See application file for complete search history.

(56) References Cited

U.S. PATENT DOCUMENTS

| | | | |
|---|---|---|---|
| 4,844,613 A | 7/1989 | Batchelder et al. | |
| 4,889,427 A | 12/1989 | Van Veen et al. | |
| 4,997,278 A | 3/1991 | Finlan et al. | |
| 5,917,608 A | 6/1999 | Naya et al. | |
| 7,692,795 B2 | 4/2010 | Sasaki et al. | |
| 8,024,279 B2 | 9/2011 | Ryhanen et al. | |
| 8,354,296 B2 | 1/2013 | Dimitrakopoulos et al. | |
| 8,363,223 B2 | 1/2013 | Ran et al. | |
| 8,395,774 B2 | 3/2013 | Afzali et al. | |
| 8,664,642 B1 | 3/2014 | Davis | |
| 2010/0020327 A1* | 1/2010 | Fattal et al. | 356/445 |

(Continued)

FOREIGN PATENT DOCUMENTS

| | | |
|---|---|---|
| EP | 0863395 A2 | 9/1998 |
| WO | 2010122776 A1 | 10/2010 |
| WO | 2011142118 A1 | 11/2011 |

OTHER PUBLICATIONS

W. Gao et al., "Excitation of plasmonic waves in graphene by guided-mode resonances," ACS Nano, vol. 6, No. 9, Aug. 2012, pp. 7806-7813.

(Continued)

*Primary Examiner* — Tri T Ton
(74) *Attorney, Agent, or Firm* — Cantor Colburn LLP; Vazken Alexanian

(57) ABSTRACT

Embodiments are directed to a plasmonic structure having an enhanced resonance frequency bandwidth. In one aspect, a plasmon-enhanced coupler is provided having a first plasmon region and a second plasmon region. A resonance frequency bandwidth of the plasmon-enhanced coupler is a hybridization of at least one first resonance frequency of the first plasmon region, and at least one second resonance frequency of the second plasmon region. The first plasmon region may be implemented as a single layer of graphene conductive material, and the second plasmon region may be implemented as multiple layers of graphene conductive material. The resonance frequency bandwidth may be chosen to overlap a frequency that comprises a vibration frequency of certain molecules of interest. Radiation directed to the plasmon-enhanced coupler causes its plasmons to interact with the molecules of interest, thereby altering the radiation.

19 Claims, 17 Drawing Sheets

(56) References Cited

U.S. PATENT DOCUMENTS

2012/0134880 A1 5/2012 Kurkina et al.
2013/0029430 A1 1/2013 Tamura et al.

OTHER PUBLICATIONS

J. Homola, "Surface Plasmon Resonance Sensors for Detection of Chemical and Biological Species," Chemical Reviews, vol. 108, No. 2, 2008, pp. 462-493.
J. Homola et al., "Surface Plasmon Resonance Sensors: Review," Sensors and Actuators B: Chemical, vol. 54, No. 1, 1999, pp. 3-15.
L. Ju et al., "Graphene plasmonics for tunable terahertz metamaterials," Nature Nanotechnology, vol. 6, No. 10, Sep. 2011, pp. 630-634.
Y. Li et al., "Graphene plasmon enhanced vibrational sensing of surface-adsorbed layers," Nano Letters, vol. 14, No. 3, Feb. 2014, pp. 1573-1577.
Phaedon Avouris et al., pending U.S. Appl. No. 14/313,456 entitled "Chemical Sensors Based on Plasmon Resonance in Graphene," filed with the U.S. Patent and Trademark Office on Jun. 24, 2014.

* cited by examiner

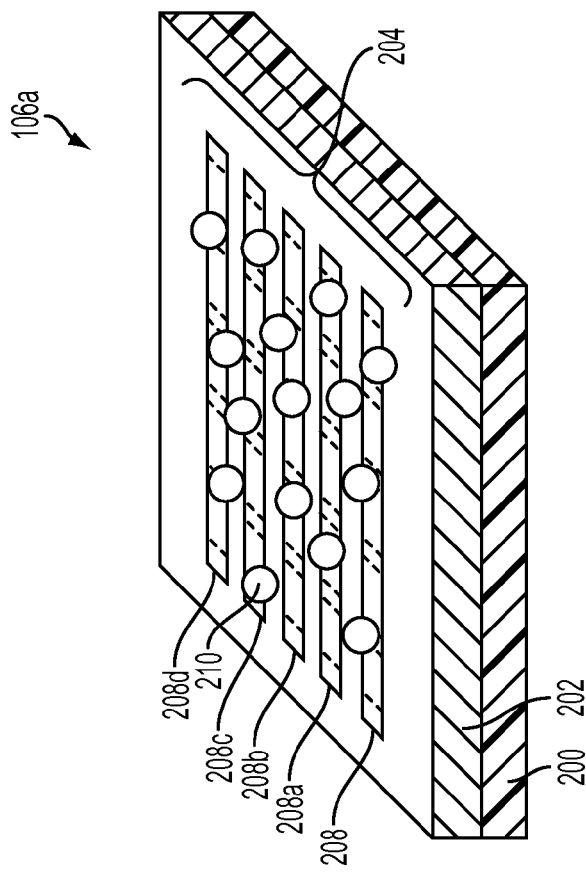
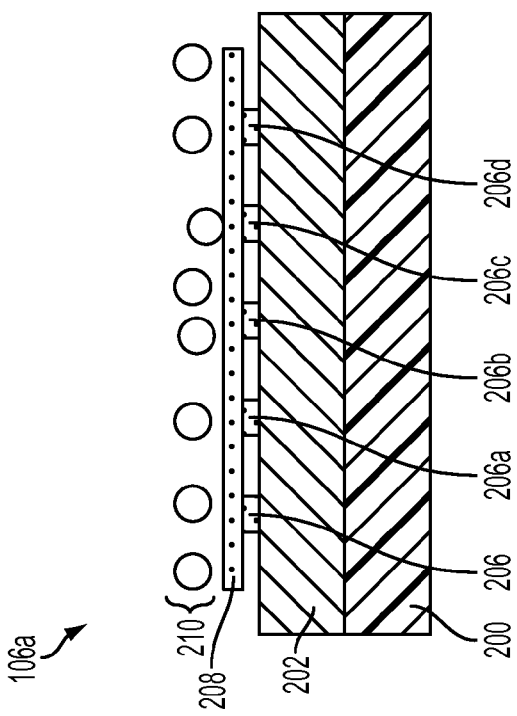
FIG. 2B
FIG. 2A

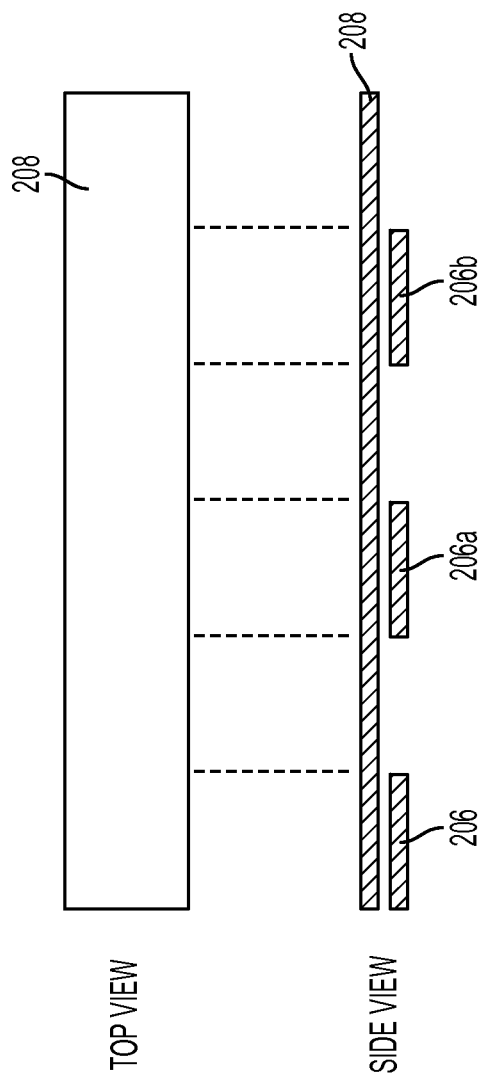

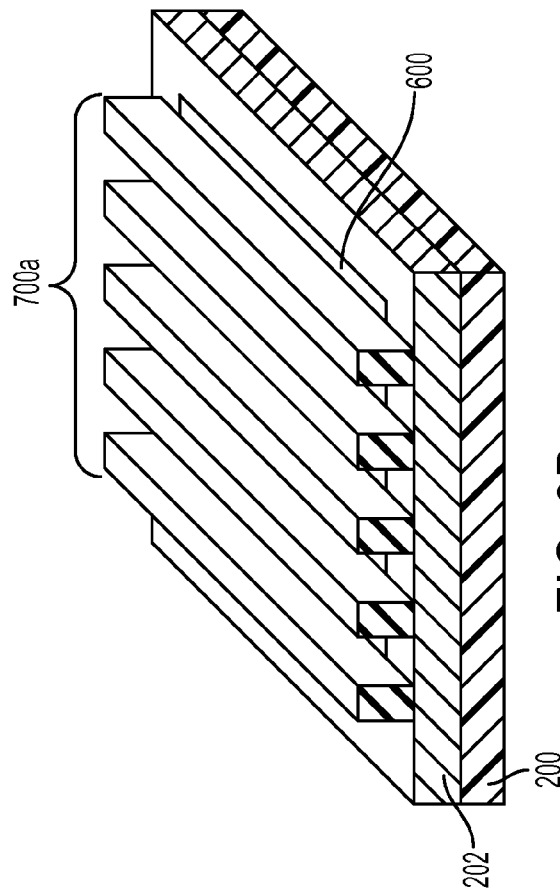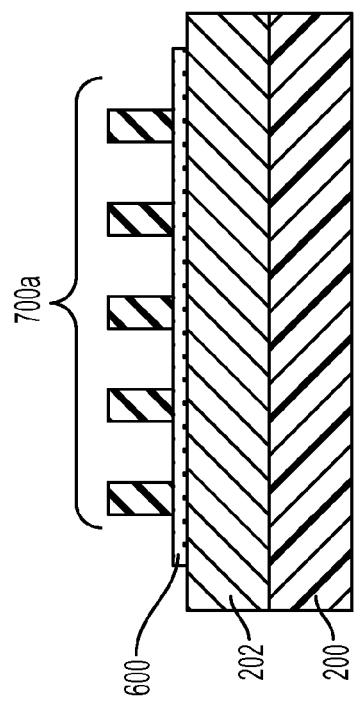
FIG. 8B
FIG. 8A

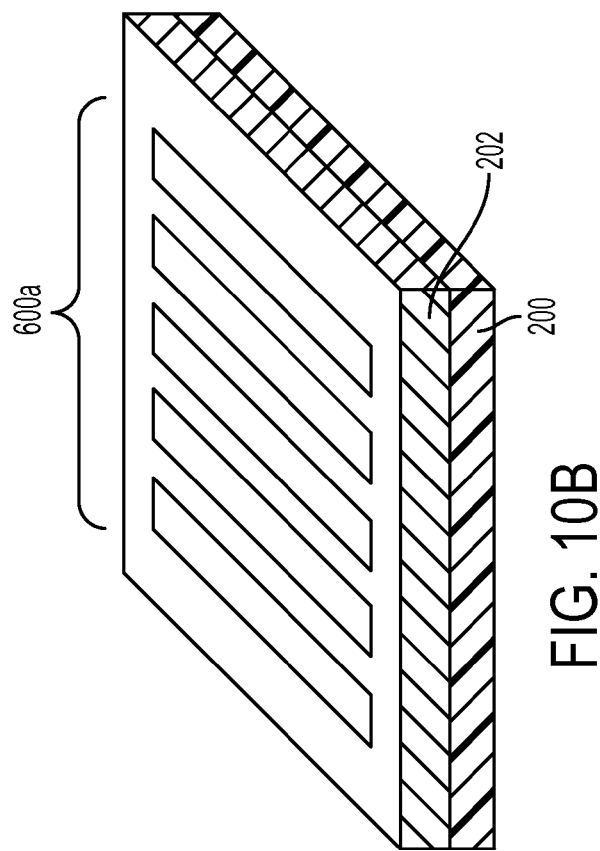
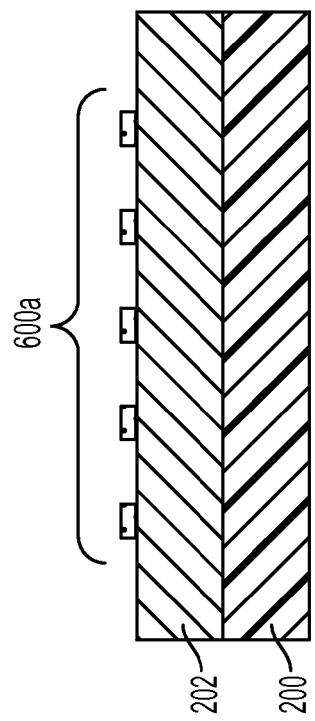
FIG. 10B
FIG. 10A

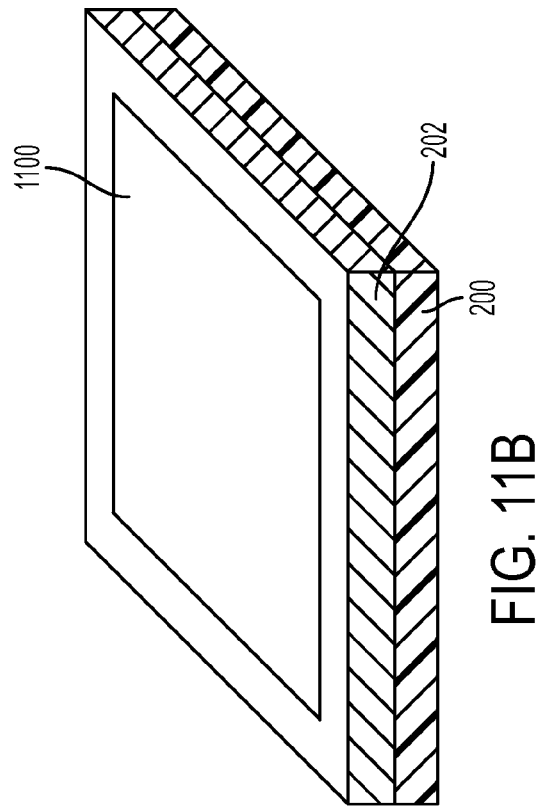
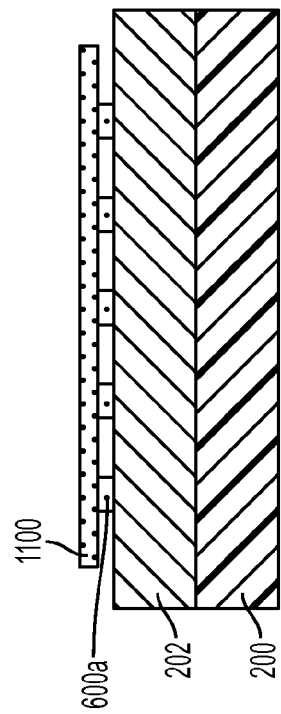
FIG. 11B
FIG. 11A

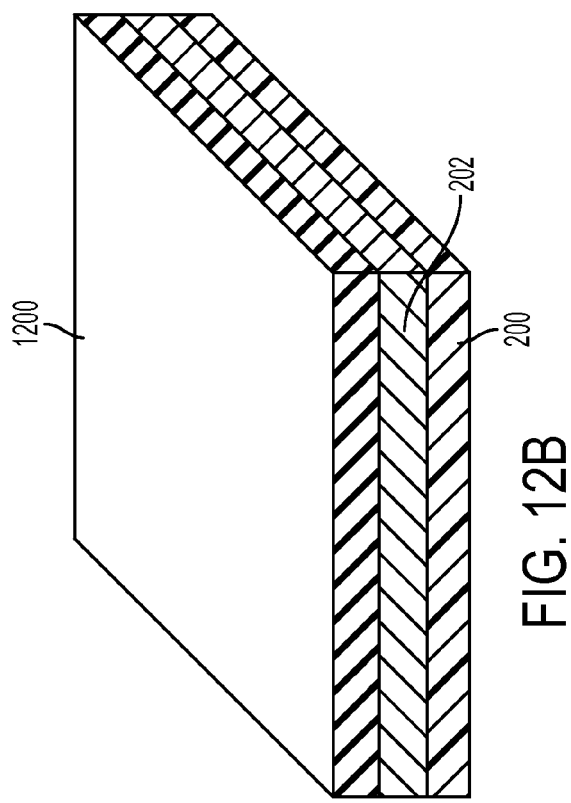
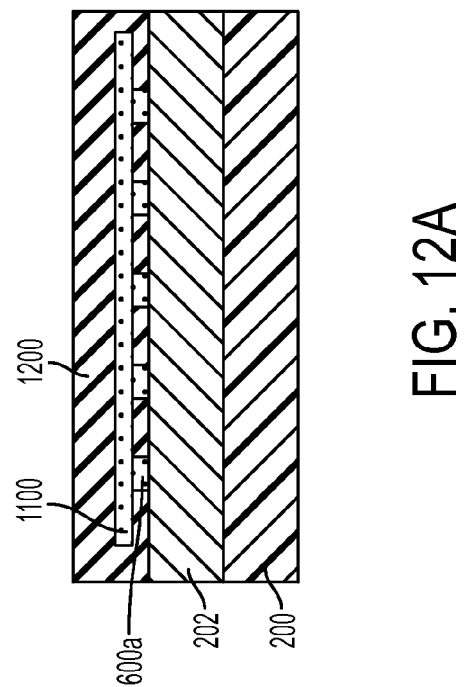
FIG. 12A
FIG. 12B

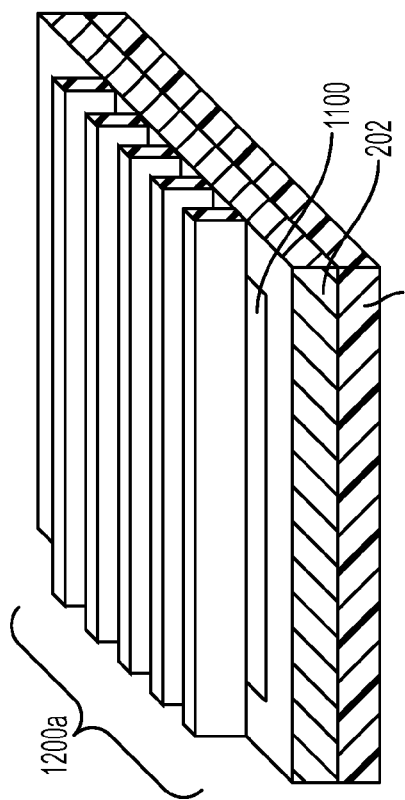
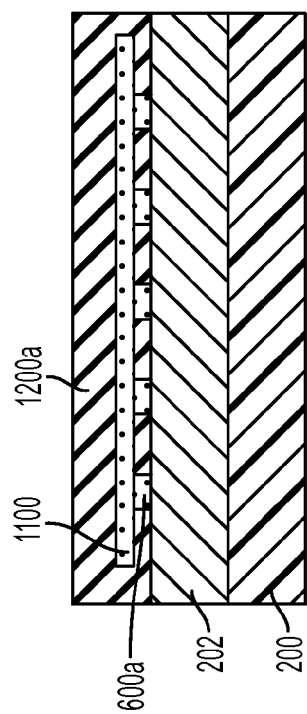
FIG. 13B
FIG. 13A

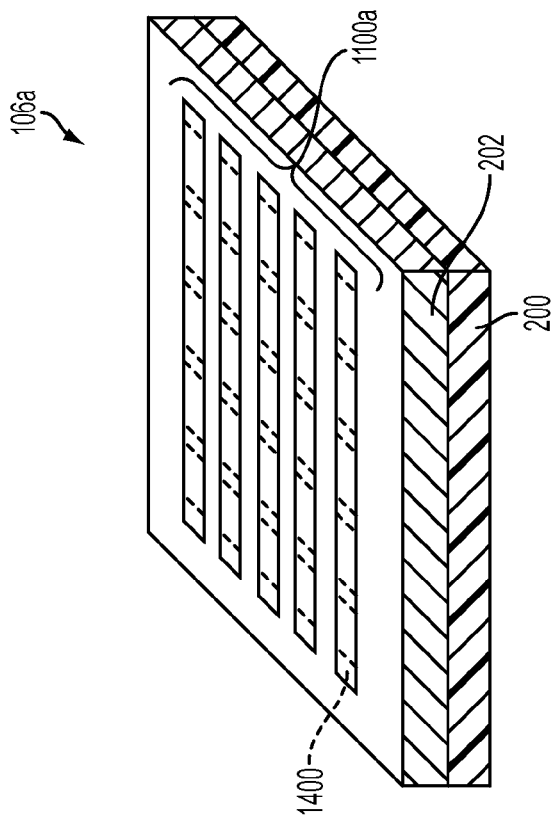
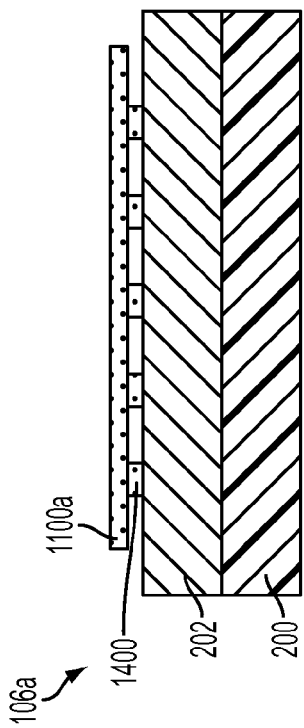
FIG. 15B
FIG. 15A

PLASMONIC STRUCTURE WITH ENHANCED BANDWIDTH

BACKGROUND

The present disclosure relates in general to the enhancement of a plasmonic structure's bandwidth to improve its overall performance. More specifically, the present disclosure relates to using the enhanced bandwidth plasmonic structure in a variety of optoelectronic applications, including analyzing chemical and biological samples.

Surface plasmons are produced from the interaction of optical energy with a conductive material at a metal-dielectric interface. Under specific conditions, the incident optical energy couples with the conductive material to create self-sustaining, propagating electromagnetic waves known as surface plasmons. Once launched, surface plasmons ripple along the metal-dielectric interface and do not generally stray from this narrow path.

Surface plasmon resonance (SPR) sensing is a powerful and quantitative system and methodology for identifying the interactions of a variety of chemical and biological processes. SPR sensing provides a means for not only identifying chemical and biological interactions and quantifying their kinetic and energetic properties, but also for performing very sensitive detection of chemical and biological substances. Contemporary SPR sensing may be accomplished using plasmons generated at a metal/dielectric interface, with the metal typically being gold. See, for example, J. Homola et al., "Surface Plasmon Resonance Sensors: Review," Sensors and Actuators B: Chemical 54, 3 (1999).

For chemical/biological sensing/detecting applications, the plasmon resonance frequency must have sufficient overlap with the characteristic vibration frequency of the molecule of interest in order to achieve the necessary interaction between the plasmons and the molecule of interest. Thus, when used in SPR sensing, an important design goal for plasmonic structures is providing sufficient overlap between the plasmon resonance frequency and the vibration frequency of the molecule of interest. This overlap of the two frequencies is known generally as frequency matching. In practice, it can be difficult to fabricate a conducting material having plasmons at a specific resonance frequency because the factors that shift plasmon resonance frequency are numerous and relatively difficult to control.

SUMMARY

Embodiments are directed to a plasmon-enhanced coupler comprising a first plasmon region and a second plasmon region. A resonance frequency bandwidth of the plasmon-enhanced coupler comprises a hybridization of at least one first resonance frequency of the first plasmon region and at least one second resonance frequency of the second plasmon region.

Embodiments are further directed to a system for analyzing a plasmon resonance of a coupler comprising a light source that transmits light to the coupler. The system includes the coupler and a detector. The coupler comprises a first plasmon and a second plasmon. The detector converts light received from the coupler to an electrical signal. A resonance frequency bandwidth of the coupler comprises a hybridization of a first resonance frequency of the first plasmon and a second resonance frequency of said second plasmon.

Embodiments are further directed to a method of forming a plasmon-enhanced coupler, the method comprising forming a first plasmon region, and forming a second plasmon region. A resonance frequency bandwidth of the plasmon-enhanced coupler comprises a hybridization of at least one first resonance frequency of the first plasmon region and at least one second resonance frequency of said second plasmon region.

Additional features and advantages are realized through the techniques described herein. Other embodiments and aspects are described in detail herein. For a better understanding, refer to the description and to the drawings.

BRIEF DESCRIPTION OF THE SEVERAL VIEWS OF THE DRAWINGS

The subject matter which is regarded as embodiments is particularly pointed out and distinctly claimed in the claims at the conclusion of the specification. The foregoing and other features and advantages of the embodiments are apparent from the following detailed description taken in conjunction with the accompanying drawings in which:

FIG. 2A depicts a two-dimensional block diagram illustrating additional detail of a plasmon-enhanced coupler in accordance with one or more embodiments;

FIG. 2B depicts a three-dimensional view of the block diagram shown in FIG. 2A;

FIG. 2C depicts top and side views of a nanoribbon configuration of the plasmon-enhanced coupler shown in FIGS. 2A and 2B;

FIG. 8A is a two-dimensional diagram illustrating ribbon structures patterned into the resist according to one or more embodiments;

FIG. 8B is a three-dimensional view of the diagram shown in FIG. 8A;

FIG. 10A is a two-dimensional diagram showing the resist having been removed, leaving a first layer of patterned graphene ribbons on the surface according to one or more embodiments;

FIG. 10B is a three-dimensional view of the diagram shown in FIG. 10A;

FIG. 11A is a two-dimensional diagram showing a second layer of graphene deposited on the first layer of patterned graphene ribbons according to one or more embodiments;

FIG. 11B is a three-dimensional view of the diagram shown in FIG. 11A;

FIG. 12A is a two-dimensional diagram illustrating another lithography resist coated on the surface according to one or more embodiments;

FIG. 12B is a three-dimensional view of the diagram shown in FIG. 12A;

FIG. 13A is a two-dimensional diagram showing ribbon structures patterned into the resist such that the orientation of the resist ribbons are perpendicular to the first layer of graphene ribbons according to one or more embodiments;

FIG. 13B is a three-dimensional view of the diagram shown in FIG. 13A;

FIG. 15A is a two-dimensional diagram showing the resist removed, leaving a second layer of patterned graphene ribbons, thereby completing a structure having a first and second layer of graphene that combine to form a graphene ribbon structure with periodic, alternating one and two layer regions according to one or more embodiments;

FIG. 15B is a three-dimensional view of the diagram shown in FIG. 15A; and

Figure 1:
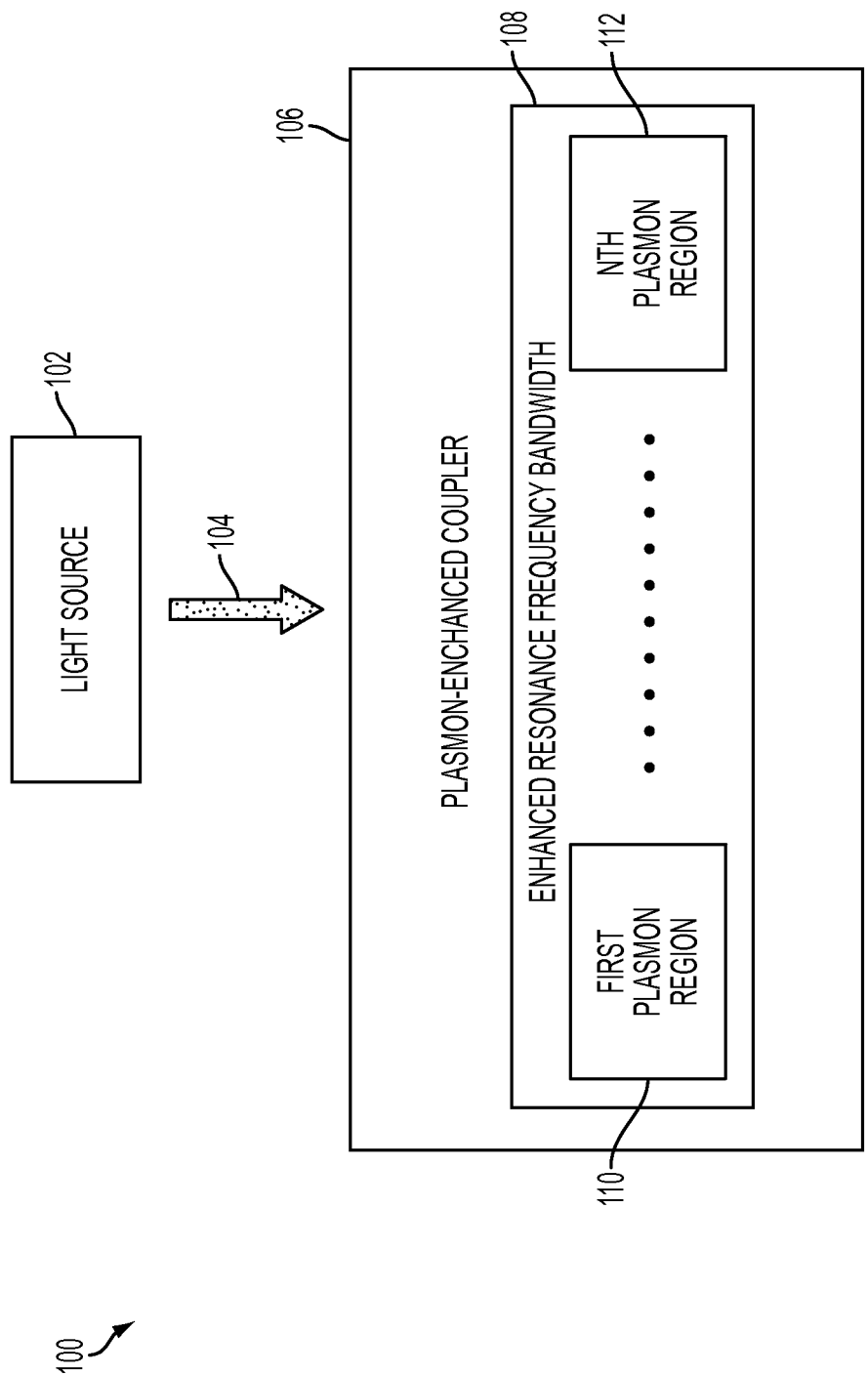
FIG. 1 depicts a block diagram illustrating a system having a plasmon-enhanced coupler in accordance with one or more embodiments.

In the accompanying figures and following detailed description of the disclosed embodiments, the various elements illustrated in the figures are provided with three digit reference numbers. The leftmost digit of each reference number corresponds to the figure in which its element is first illustrated.

DETAILED DESCRIPTION

The present disclosure and exemplary embodiments described herein provide structures, systems and methodologies for enhancing or widening the bandwidth of a plasmon-enhanced coupler, which may be used in a variety of optoelectronic applications, including for example, chemical and biological sensing and/or detection systems. Another example of an optoelectronic application for the disclosed plasmon-enhanced coupler is utilizing it to implement a notch filtering function.

With specific reference to chemical and/or biological sensing and detecting applications, a necessary feature is that the plasmon resonance frequency must couple with an intrinsic vibration frequency of the substance of interest. In other words, the plasmon resonant peak must overlap closely with the vibration mode of the substance of interest. As these plasmon peaks can be narrow, and non-idealities inherent with sample fabrication can cause resonant frequency shifting, sufficient overlap with the vibration of the target molecule can be challenging. The present disclosure alleviates this constraint by intentionally increasing the bandwidth of the plasmon peak, i.e., making the resonant peak broader. Having a broader plasmon resonance bandwidth increases the likelihood of overlap with the vibration of the target molecule, hence enhancing the detection and sensing performance of conductive materials such as graphene plasmons.

In one or more embodiments of the present disclosure, a practical scheme to fabricate chemical and biological sensing platforms based on plasmon resonance in graphene with enhanced plasmon bandwidth is proposed. In one or more disclosed embodiments, the charge carrier concentration in graphene is localized in such a way as to promote plasmon excitation, and graphene layers are stacked in such a way as to promote bandwidth enhancement. To summarize the process, which is described in greater detail later in this disclosure, a first layer of graphene is placed on a substrate and its charge concentration is physically confined. Within the confining structures, the number of subsequent graphene layers is periodically iterated until the confining structure includes a plurality of plasmon regions wherein each plasmon region has a different number of layers, and hence a different plasmon resonance frequency, than the adjacent plasmon region. The plasmon regions are sufficiently close that their individual resonance frequencies interact to form an enhanced resonance frequency bandwidth that is a hybridization of the individual resonance frequencies generated by each plasmon region. Graphene plasmons of this structure are excited by incident light, and the plasmons interact with vibration dipole moments in test species deposited on the platform surface in such a way as to modulate the output signal of the light transmitted through the platform. This modulation can be constructive or destructive, is seen in the absorption spectrum of the outgoing light signal, and allows for sensitive identification of molecular compounds associated with chemical and/or biological species. Due to the iterative stacking of the graphene layers within the graphene plasmonic structure, the resulting bandwidth of the resonant peak is broadened or enhanced. The enhanced bandwidth of the resonant peak allows for a wider range of frequencies to be probed.

As additional technical background, a more detailed description of plasmons will now be provided. Plasmons are a collective excitation of the electronic "fluid" in a piece of conducting material, analogous to the way that ripples on the surface of a pond are a collective mode of the water molecules of the liquid. If one pushes down on the surface of a pond at one location with a float, the density of the water does not change. Instead, water elsewhere is displaced because the water molecules have finite volume and push each other out of the way. The electronic fluid of a conducting material acts similarly, not because of any finite size or even the Coulomb repulsion of the electrons, but mostly because of the Pauli Exclusion Principle, which tends to keep the electrons out of each others' way.

Plasmons, which may be thought of as "electronic ripples," can have a well-defined wavelength because when the electrons are displaced, the positive charge left behind exerts an attractive force on the electrons, trying to pull them back to their original positions. This interaction is what makes the plasmons oscillate once they're excited, and these Coulomb interactions are also why plasmons cost energy to excite. These Coulomb interactions with the positive background charge also force plasmons to obey certain boundary conditions at the edges of the host conducting material. As a result, nanoparticles can have discrete allowed plasmonic modes strongly influenced by particle shape, while larger structures (e.g., thin metal films) can have propagating plasmon modes over a broad range of wavelengths. Plasmons decay into incoherent electron-hole pair excitations, eventually dissipating their energy as the moving electrons begin to scatter instead of oscillating smoothly.

The above-described characteristics of plasmons allow them to have a variety of applications, including offering a way of shuttling information around on computer chips that naturally interfaces with optics. Plasmons are also associated with large local electric fields at conductive surfaces, which can be very useful for certain kinds of spectroscopies. In properly designed plasmonic materials, plasmon properties can be manipulated so that the overall optical response of a conducting system can be tuned.

Although the present disclosure applies to plasmons of any type of conductive material, one or more disclosed embodiments focus on graphene as the conductive material. Several factors make graphene a unique platform for plasmon-enhanced couplers used in infrared spectroscopy: (1) graphene has a two-dimensional lattice structure, which allows for a very high plasmon confinement field that cannot be achieved with metal-based plasmons, thus promising high sensitivity; (2) the charge concentration profile can be patterned in graphene using standard techniques; and (3) the excitation and coupling to surface plasmons in the resulting structure can be easily achieved. The high carrier mobility and conductivity that are facilitated by the lattice structure of graphene allow for high plasmon field confinement and large plasmon propagation lengths as compared to more conventional gold surfaces of similar thickness. Also, plasmon resonances in graphene can be generated/coupled directly to light by physical confinement of the charge oscillations or by attaching graphene to a dielectric grating. Physical confinement can be achieved by routine oxygen plasma etching, and dielectric grating substrates can be engineered using conventional complementary metal-oxide semiconductor (CMOS) fabrication techniques. Lastly, the plasmon resonance frequency of graphene is in the infrared regime, where most chemicals have their characteristic vibration signals. This makes graphene a natural fit for chemical sensing applications.

Additional details of graphene-based SPR sensor devices and fabrication methodologies are disclosed in a co-pending, commonly assigned U.S. patent application entitled "CHEMICAL SENSORS BASED ON PLASMONIC RESONANCE IN GRAPHENE," filed Jun. 24, 2014 and having application Ser. No. 14/313,456. The entire disclosure of this application is incorporated herein by reference.

Turning now to the drawings in greater detail, wherein like reference numerals indicate like elements, FIG. 1 depicts a block diagram of a system 100 including a light source 100, a plasmon-enhanced coupler 106, an enhanced resonance frequency bandwidth 108, a first plasmon region 110 and an Nth plasmon region 112, configured and arranged as shown. Enhanced resonance frequency bandwidth 108 is provided by the 1-to-N plasmon regions, represented by first plasmon region 110 and $N^{th}$ plasmon region 112. Thus the total number (N) of plasmon regions is at least two, with the upper limit dictated by practical device constraints for the particular application. For a two plasmon region implementation, each plasmon region 110, 112 generates an individual resonance frequency having an individual peak frequency and an individual bandwidth. Under the present disclosure, plasmon regions 110, 112 are placed in sufficiently close proximity that they interact to create an enhanced resonance frequency bandwidth that is a hybridization of the individual resonance frequency of each plasmon region 110, 112. Specifically, the resulting peak of the enhanced resonance frequency is somewhere between the peak individual resonance frequencies of each plasmon region 110, 112, and the resulting bandwidth of the enhanced resonance frequency is broader than the individual resonance frequency bandwidth of each plasmon region 110, 112. The enhanced resonance frequency bandwidth may be adjusted by adjusting the spacing between plasmon regions 110, 112.

As described in more detail later in this disclosure, each plasmon region 110, 112 may be implemented as graphene conductive material having a selected number of layers, wherein the number of layers in a given plasmon region is different from the number of layers in an adjacent plasmon region. In general, the resonance frequency characteristic of a given conductive material is based on a number of factors including the number of layers in the conductive material. Thus, plasmon region 110 may be implemented, for example, as a graphene region having a single layer, and plasmon region 112 may be implemented, for example, as a graphene region having multiple layers. Where more than two plasmon regions are provided, the plasmon regions would alternate between a first layer profile (e.g., a single layer) and a second layer profile (e.g., multiple layers) such that each plasmon region is adjacent to a plasmon region having a different layer profile (i.e., a different number of layers).

Figure 4:
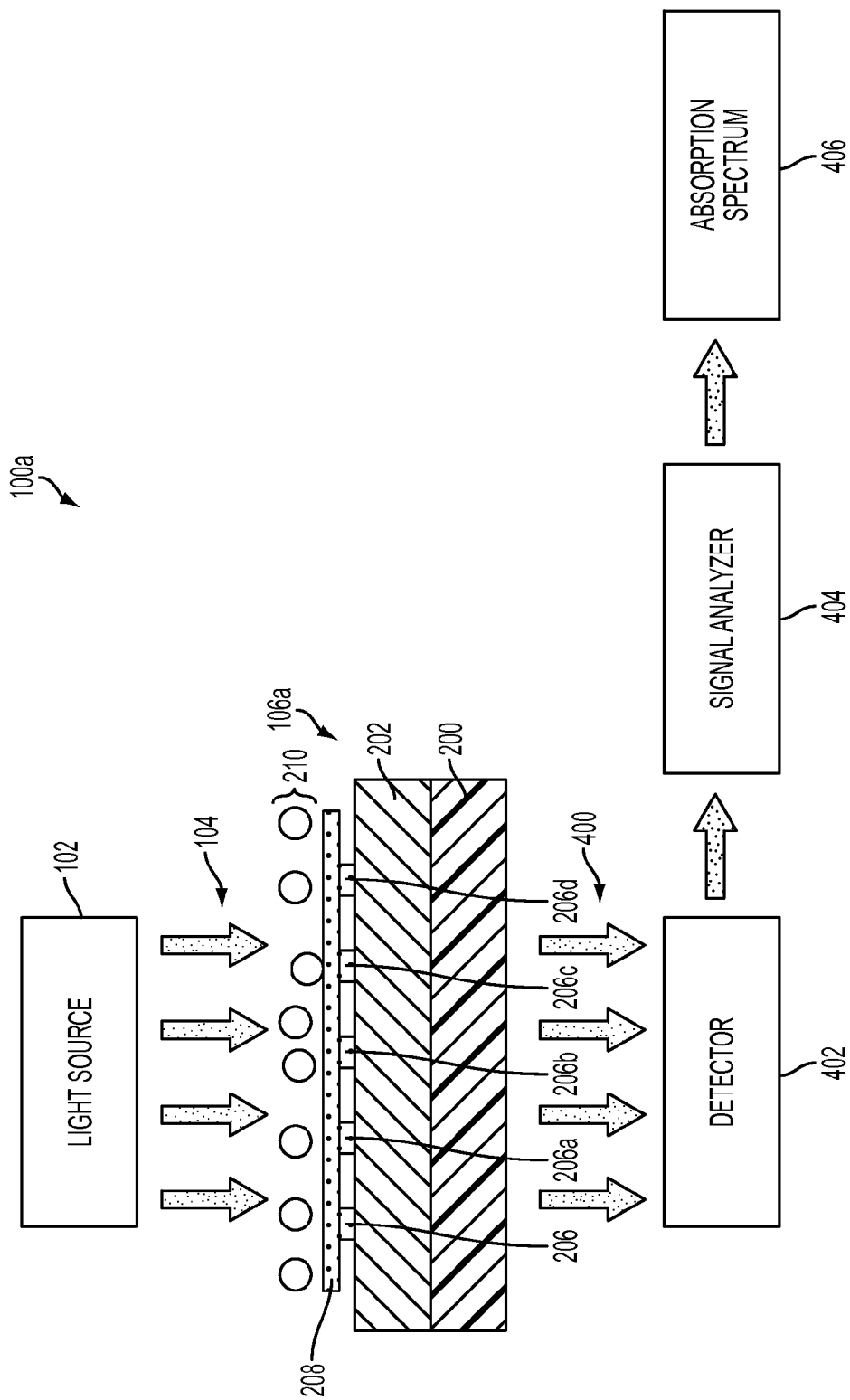
FIG. 4 depicts a diagram illustrating a system that uses a disclosed plasmon-enhanced coupler to analyze a sample in accordance with one or more embodiments.
Figure 5:
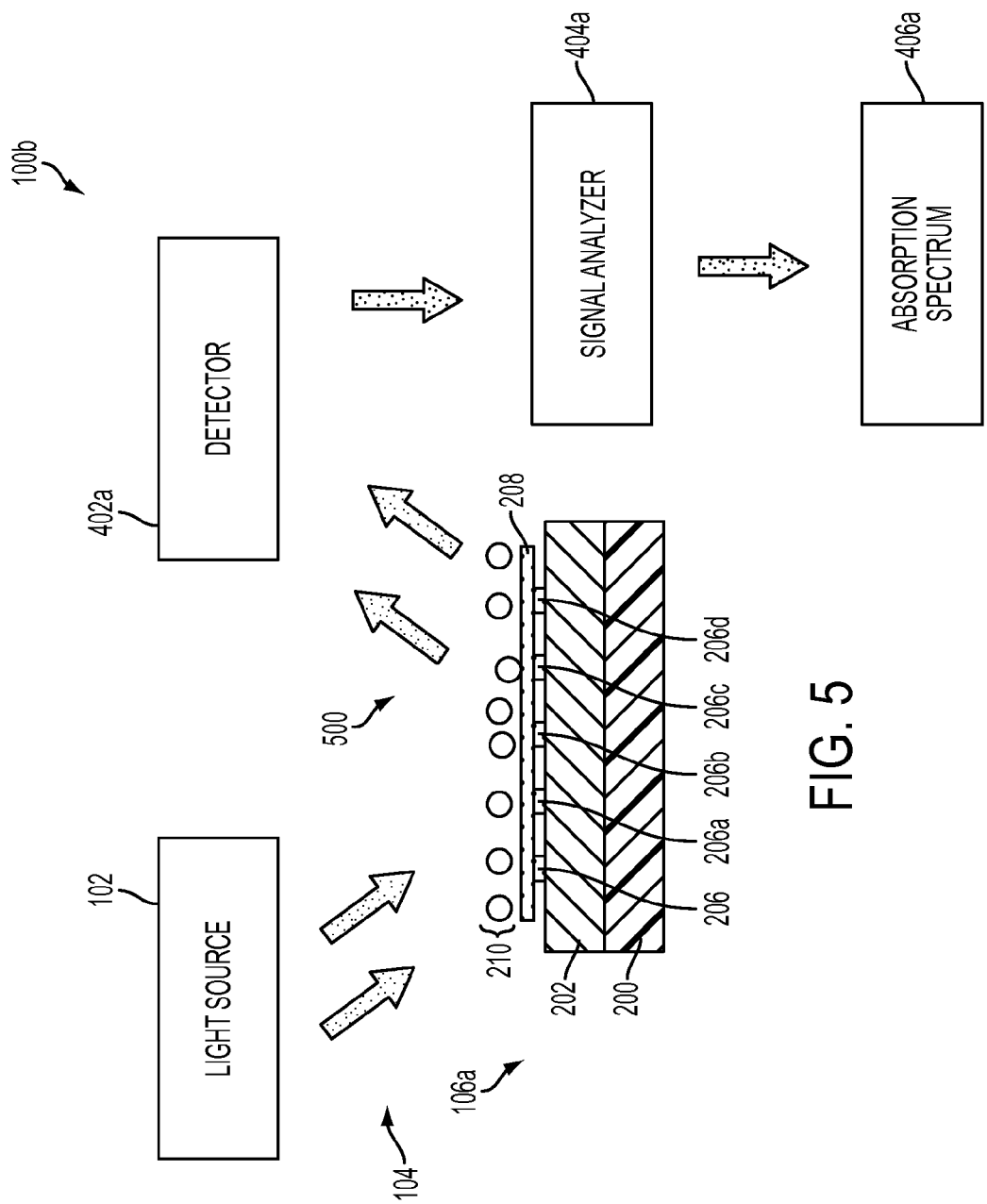
FIG. 5 depicts a diagram illustrating an alternative system that uses a disclosed plasmon-enhanced coupler to analyze a sample in accordance with one or more embodiments.

System 100 has a variety of potential applications in a variety of optoelectronic systems. For example, system 100 and plasmon-enhanced coupler 106 may be used to implement a chemical or biological sensing and detection function. In a chemical/biological sensing/detection platform, incident light 104 excites plasmon regions 110, 112 to generate plasmons that can interact with vibrational dipole moments in test species (not shown) deposited on coupler 106. This interaction modulates incident light 104 and may be constructive or destructive, thereby allowing for sensitive identification of molecular compounds associated with chemical and/or biological species. More detailed examples of chemical/biological sensing/detection platforms for system 100 are shown in FIGS. 4 and 5 and described later in this disclosure.

Another potential application of system 100 and plasmon-enhanced coupler 106 is in the performance of an optical filtering function such as a notch-type filter. For a notch filter application, plasmon regions 110, 112 are designed to target a bandwidth of interest in incident light 104. Thus, incident light in the resonance frequency bandwidth of coupler 106 would be attenuated, and incident light outside the resonance frequency bandwidth of coupler 106 would be undisturbed.

Focusing again on the chemical/biological sensing/detecting application of coupler 106, FIGS. 2A, 2B and 2C provide a more detailed illustration of a periodic, multiple-layer implementation of coupler 106 shown in FIG. 1. FIG. 2A is a block diagram showing a two-dimensional, cross-sectional view of an enhanced coupler 106a in accordance with one or more embodiments. FIG. 2B is a three-dimensional view of the block diagram shown in FIG. 2A. FIG. 2C is a top view and side view of a nanoribbon configuration of the plasmon-enhanced coupler 106a shown in FIGS. 2A and 2B. As best shown in FIGS. 2A and 2B, plasmon-enhanced coupler 106a includes a conducting backplane 200, a layer of insulating material 202, a ribbon array 204, a first layer of nanoribbon sections 206, 206a, 206b, 206c, 206d and a second layer of nanoribbons 208, 208a, 208b, 208c, 208d, configured and arranged as shown. The term "nanoribbon" as used herein generally refers to strips of graphene each having a width of from about 50 nm to about 300 nm, and ranges therebetween. Because the graphene nanoribbons are to be patterned from graphene layer 102, each of the nanoribbons likewise will consist of from about 1 (a monolayer) up to a stack of about 5 sheets of graphene and ranges therebetween.

Insulating dielectric layer 202 is deposited on conducting backplane layer 200. A suitable material for forming conducting backplane layer 200 includes, but is not limited to, intrinsic silicon. As described in more detail later in this disclosure, one or more embodiments use a so-called transmission measurement to analyze a sample by passing light through the sample and coupler 106a. For transmission measurements, intrinsic silicon is ideal because it is transparent in the correct spectral range and can also be used as an electrostatic gate electrode. Alternatively, conventional gate metals might be employed. For example, tantalum, titanium, platinum and/or tungsten may be used in forming conducting backplane layer 200. However, because these gate metals are not transparent to light, configurations of coupler 106a employing a metal back gate would need to be read via a reflection measurement. Any insulating dielectric would be a suitable material for forming insulating dielectric layer 202. Examples include, but are not limited to, gate dielectrics such as silicon dioxide and aluminum oxide, and high-K dielectrics such as hafnium oxide or lanthanum oxide.

As previously described in connection with FIG. 1, plasmon-enhanced coupler 106 includes an enhanced resonance frequency bandwidth 108 formed from various plasmon regions 110, 112. In FIGS. 2A to 2C, the plasmon regions are implemented as nanoribbons 208, 208a, 208b, 208c, 208d, each having alternating sections of one-layer graphene and two-layer graphene. The one-layer graphene sections comprise a top layer formed by the graphene nanoribbon 208, and the two-layer graphene sections comprise graphene nanoribbon 208 over a first layer of nanoribbon sections 206, 206a, 206b, 206c, 206d. The actual number of graphene layers in each plasmon region 110, 112 is not critical as long as the number of layers in a given plasmon region (e.g., 110) is different from the number of layers in a plasmon region adjacent thereto (e.g., 112).

Figure 3:
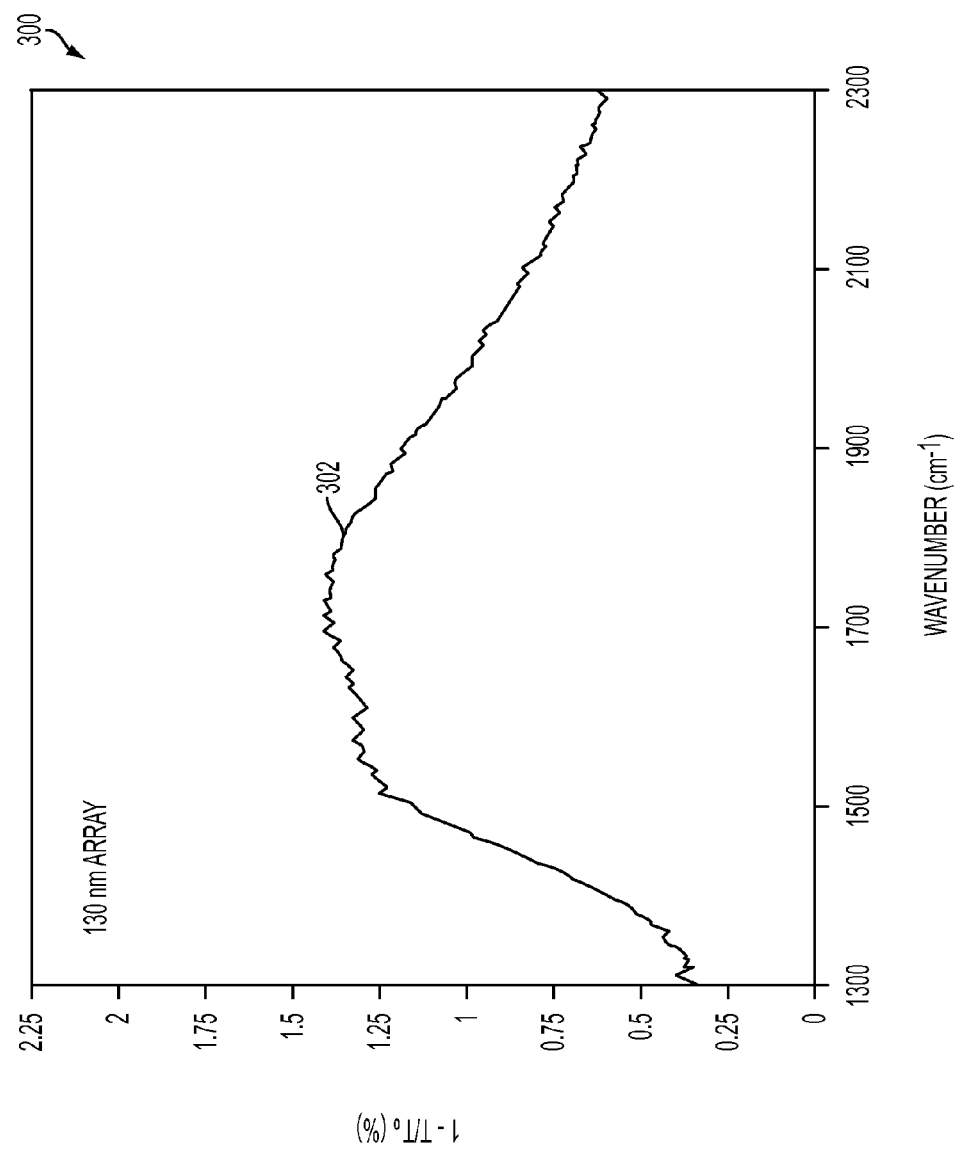
FIG. 3 depicts a graph illustrating the plasmon resonance of the nanoribbon design shown in FIGS. 2A-2C.

FIG. 3 is a graph 300 illustrating the enhanced plasmon absorption 302 of the nanoribbon design shown in FIGS. 2A-2C. As shown, the bandwidth of enhanced plasmon absorption 302 is relatively wide, extending from about 1500 $cm^{-1}$ to about 2000 $cm^{-1}$ where the absorption percentage (shown along the vertical y-axis) is above approximately 1. The broadened bandwidth near the resonant peak allows for a wider range of frequencies to be probed, makes it easier to match coupler frequency with molecules of interest, and relaxes other design parameters that would otherwise need to be more tightly controlled in order to achieve frequency matching in the absence of plasmon-enhanced bandwidth provided by the present disclosure.

Exemplary methods of using plasmon-enhanced coupler 106a for analyzing a sample are now described by way of reference to systems 100a and 100b shown in FIGS. 4 and 5. By way of example only, plasmon-enhanced coupler 106a will be used in the figures to illustrate the implementation process. However, the same process may be performed in the same manner using the more general plasmon-enhanced coupler 106 shown in FIG. 1.

FIG. 4 illustrates a chemical/biological sensing/detecting system 100a having light source 102 that produces incident light 104, plasmon-enhanced coupler 106a, conducting backplane 200, insulating material 202, first layer nanoribbon sections 206, 206a, 206b, 206c, 206d, second layer nanoribbon 208, a sample of chemical/biological species 210, refracted/transmitted light 400, a detector 402, a signal analyzer 404 and an absorption spectrum 406, arranged and configured as show. Systems 100a and 100b may employ a fourier transform infrared (FTIR) spectroscopy setup in conjunction with plasmon-enhanced coupler 106a wherein a broadband lamp is used as light source 102 in a Michelson interferometer with a movable mirror (not shown). In general, sample 210 is applied to a graphene nanoribbon 208 of plasmon-enhanced coupler 106a, which is subsequently illuminated with a certain spectral range of light. The plasmons in graphene excited by this light interact with the vibrational dipole moments in the sample in such a way as to modulate (change) the output signal of the light transmitted through plasmon-enhanced coupler 106a. This modulation can be constructive or destructive, is seen in the absorption spectrum of the outgoing light signal, and allows for sensitive identification of molecular compounds associated with chemical and/or biological species of sample 210. As a point of reference, a baseline spectrum is preferably acquired without the graphene and sample (substrate). A spectrum with the graphene and sample is then acquired. The final spectrum data can then be given as a ratio between the sample+graphene+substrate spectrum and the substrate spectrum.

In one exemplary embodiment, sample 210 is a chemical and/or biological material of interest. For instance, plasmon-enhanced coupler 106a may be used to analyze biological samples including samples containing genetic materials (such as DNA or RNA), proteins, enzymes, cell and tissue samples, etc. Chemical sensing and analysis using plasmon-enhanced coupler 106a has a broad applicability to a wide variety of fields such as chemical compound and product testing, food analysis, drug analysis, etc. Advantageously, plasmon-enhanced coupler 106a can be used to analyze samples for which conventional analytics, such as IR spectroscopy would not be able to detect because the sample is too small.

Light source 102 is proximal to one side of plasmon-enhanced coupler 106a and sample 210. Detector 402 (e.g., an infrared detector) is proximal to an opposite side of plasmon-enhanced coupler 106a, such that incident light 104 produced by light source 102 can pass through plasmon-enhanced coupler 106a and sample 210 to detector 402. As a result, an intensity of the refracted/transmitted light 400 exiting plasmon-enhanced coupler (and which is picked up by detector 402) is altered, e.g., as compared to light exiting plasmon-enhanced coupler 106a when no sample is present. Plasmon-enhanced coupler 106a is semi-transparent to light because its components, namely graphene, conducting backplane 200 and insulating dielectric layer 202 are semi-transparent to light. Thus, a significant portion of incident light 104 may easily pass through plasmon-enhanced coupler 106a to detector 402. This configuration (i.e., light source and detector on opposite sides of plasmon-enhanced coupler 106a) assumes that plasmon-enhanced coupler 106a uses semi-transparent materials. As described above, the conducting backplane material may be intrinsic silicon, which is semi-transparent to light and can serve as an electrostatic gate electrode. Transmission measurements through plasmon-enhanced coupler 106a may then be made.

Signal analyzer 404 analyzes the electrical signal from detector 402. As known in the art, a signal analyzer is a device used to extract information from an electrical signal. In this case, the data output from signal analyzer 404 is an absorption spectrum. Suitable lightwave signal analyzers are commercially available, for example, from Agilent Technologies, Santa Clara, Calif. As highlighted above, the plasmon field generated in plasmon-enhanced coupler 106a interacts with dipole fields produced by molecular vibrations in the chemical/biological material (i.e., sample 210) of interest. This interaction results in an absorption signal modification that manifests itself as either an enhancement or reduction of the signal, and this change in the signal allows for more sensitive detection of these molecular species. Specifically, graphene plasmons and vibrational modes in the sample can interact either constructively or destructively with one another, giving either an increase or decrease in the light absorption signal (the IR absorption spectrum). Because of the relatively wide plasmon resonance frequency bandwidth provided by the disclosed plasmon-enhanced coupler 106a, the plasmon resonance frequency can be more easily matched to the dipole fields produced by molecular vibrations in the chemical/biological material (i.e., sample 210), thereby improving detection and/or sensing functions.

If the conducting backplane is constructed using metal, transmission measurements are not possible because metals are not transparent to light. In that case, reflection measurements can be made where the light source and the detector are located on the same side of plasmon-enhanced coupler 106a and proximal to the graphene. Incident light from the light source can be reflected off of the surface of plasmon-enhanced coupler 106a at an angle and captured by the detector. This alternative configuration is shown in FIG. 5, which illustrates a chemical/biological sensing/detecting system 100b having light source 102 that produces incident light 104, plasmon-enhanced coupler 106a, conducting backplane 200, insulating material 202, first layer nanoribbon sections 206, 206a, 206b, 206c, 206d, second layer nanoribbon 208, a sample of chemical/biological species 210, reflected light 500, a detector 402a, a signal analyzer 404a and an absorption spectrum 406a, arranged and configured as shown.

The same analysis process described above for system 100a of FIG. 4 is employed for system 100b of FIG. 5, except that both light source 102 and the detector 402a are located on the same side of plasmon-enhanced coupler 106a. Thus, as shown in FIG. 5, incident light 104 generated by light source 102 is reflected off of the graphene side surface of plasmon-enhanced coupler 106a having sample 210 thereon onto detector 402a. Detector 402a and signal analyzer 404a of FIG. 5 function in substantially the same way as detector 402 and signal analyzer 404 of FIG. 4 to produce an absorption spectrum.

Thus, the above-described chemical/biological sensing/detecting systems 100a, 100b, as illustrated in FIGS. 4 and 5, may be used, for example, to detect the existence of a molecule in sample 210 and also for molecular identification. It serves as a signal enhancement platform for the infrared spectroscopy (e.g., FTIR). Thus, any sample analysis performed using IR spectroscopy can be performed in conjunction with the present techniques, however, because of the relatively wide plasmon resonance frequency bandwidth provided by the disclosed plasmon-enhanced coupler 106a, the plasmon resonance frequency can be more easily matched to the dipole fields produced by molecular vibrations in the chemical/biological material (i.e., sample 210), thereby improving detection and/or sensing functions.

Figure 6A:
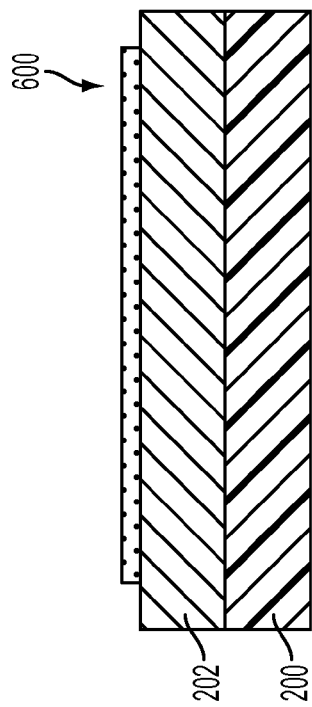
FIG. 6A is a two-dimensional diagram illustrating a starting structure for forming a graphene-based plasmon-enhanced coupler using graphene nanoribbons, the structure including a first graphene layer on a side of a dielectric layer opposite a conductive layer according to one or more embodiments.
Figure 6B:
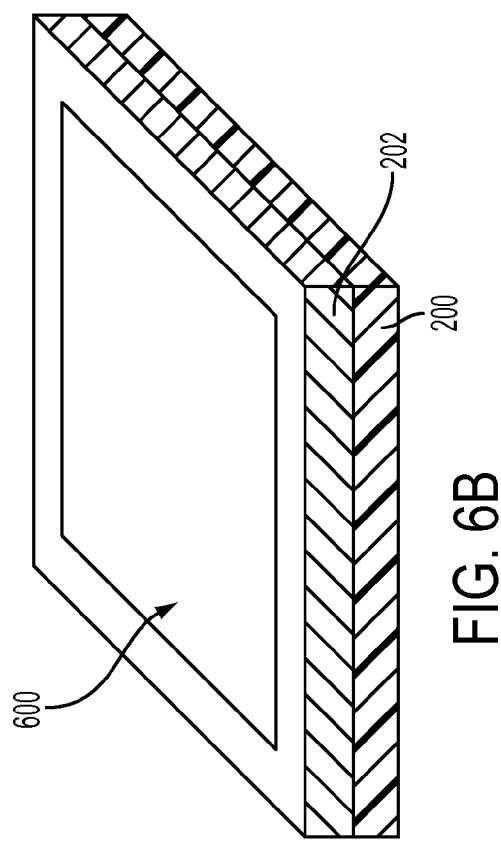
FIG. 6B is a three-dimensional view of the diagram shown in FIG. 6B.

FIGS. 6B, 6b, 7A, 7B, 8A, 8B, 9A, 9B, 10A, 10B, 11A, 11B, 12A, 12B, 13A, 13B, 14A, 14B, 15A and 15B illustrate a method of forming plasmon-enhanced coupler 106a. As shown in FIGS. 6A and 6B, a first graphene layer 600 is deposited on an insulating material/substrate 202 having a conducting backplane 200. Graphene is a material that consists of one atom thick sheets of carbon. According to an exemplary embodiment, first graphene layer 600 actually includes from 1 (i.e., a graphene monolayer) up to a stack of about 5 graphene sheets, and ranges therebetween. By way of example only, first graphene layer 600 may be deposited (or grown) on insulating material 202 using any suitable deposition process including, but not limited to, mechanical exfoliation, epitaxial growth, a transfer process and chemical vapor deposition (CVD). While exfoliation is ideal for obtaining high quality (i.e., low amount of structural defects), there are tradeoffs. For instance, the dimensions (size, thickness, etc.) of the sample are hard to control with exfoliation. Thus, processes such as CVD of graphene can be a viable alternative. A CVD process for graphene deposition is described, for example, in Mattevi et al., "A review of chemical vapour deposition of graphene on copper," J. Mater. Chem., 2011, 21, 3324-3334 (first published November 2010) (hereinafter "Mattevi"), the contents of which are incorporated by reference as if fully set forth herein. Alternatively, graphene sheets grown on another substrate (e.g., by CVD on a copper substrate—see Mattevi) can be subsequently transferred to insulating material 202. See, for example, Ko et al., "Simple method to transfer graphene from metallic catalytic substrates to flexible surfaces without chemical etching," Journal of Physics: Conference Series, Vol. 433, Issue 1 (April 2013) 012002 (hereinafter "Ko"), the contents of which are incorporated by reference as if fully set forth herein.

Figure 7B:
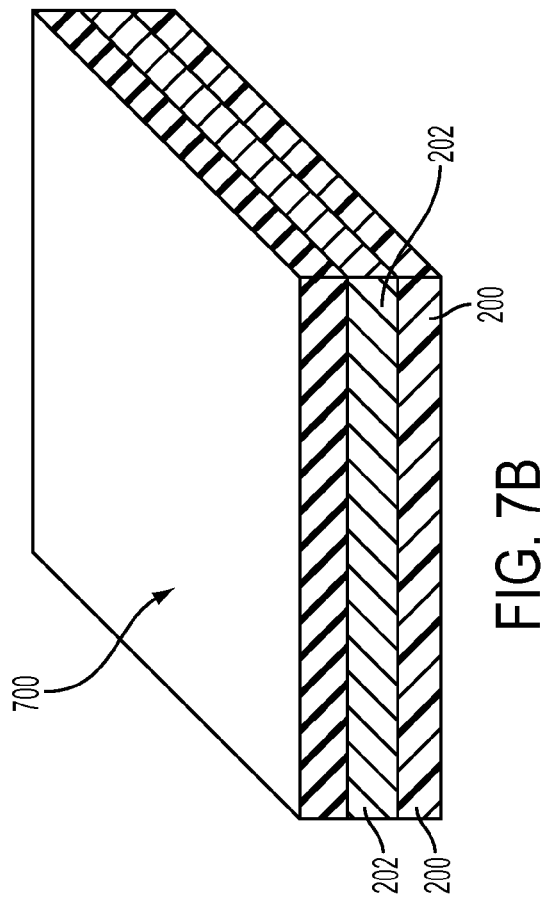
FIG. 7B is a three-dimensional view of the diagram shown in FIG. 7A.
Figure 7A:
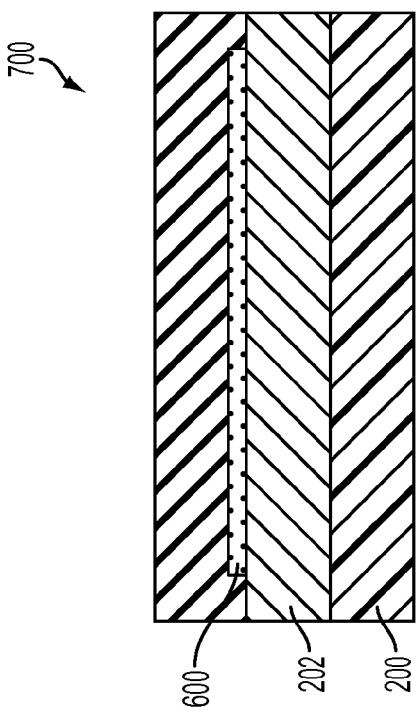
FIG. 7A is a two-dimensional diagram illustrating a lithography resist mask coated on the first graphene layer according to one or more embodiments.
Figure 9B:
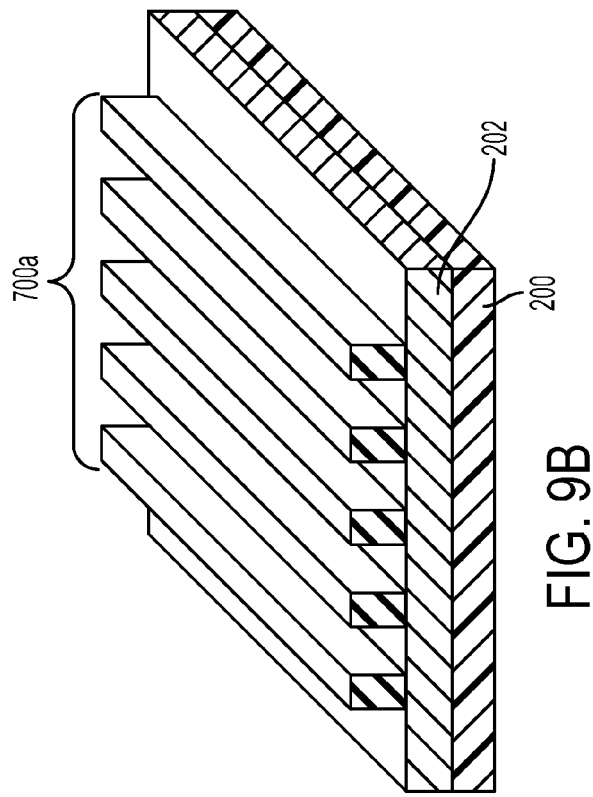
FIG. 9B is a three-dimensional view of the diagram shown in FIG. 9A.
Figure 9A:
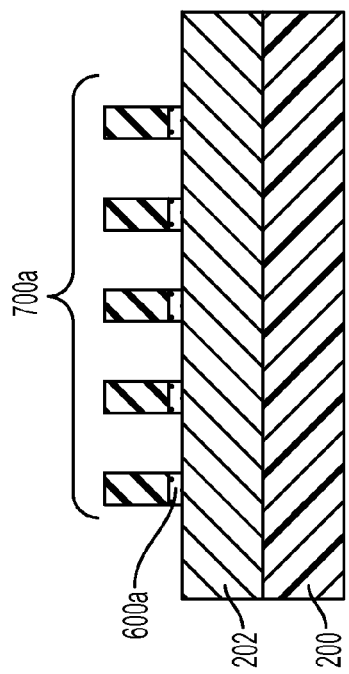
FIG. 9A is a two-dimensional diagram of the unmasked first graphene layer after etching according to one or more embodiments.
Figure 14B:
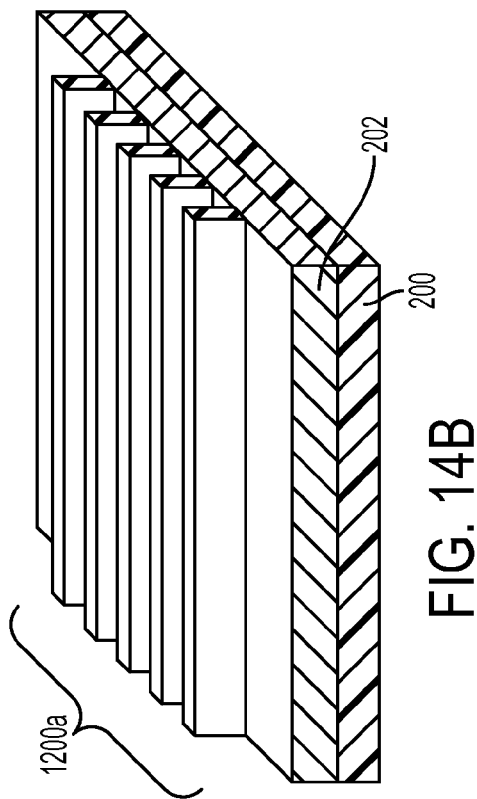
FIG. 14B is a three-dimensional view of the diagram shown in FIG. 14A.
Figure 14A:
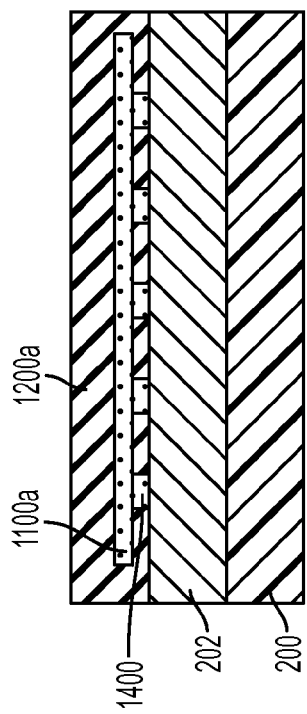
FIG. 14A is a two-dimensional diagram showing the unmasked second layer of graphene after etching according to one or more embodiments.

A lithography resist 700, such as PMMA (Polymethyl Methacrylate), is coated on the substrate surface (FIGS. 7A and 7B). Resist mask 700 is then patterned on first graphene layer 600 in the shape of ribbons 700a (FIGS. 8A and 8B). As an example, this patterning can be done by electron-beam lithography techniques. Resist ribbons 700a are used to form graphene ribbons from first graphene layer 600. An etching technique is then used to etch away the graphene that is not protected by resist ribbons 700a (FIGS. 9A and 9B). As an example, this etch can be done with oxygen reactive ion etching. Resist mask ribbons 700a are removed, leaving the exposed a first layer of graphene ribbons 600a (FIGS. 10A and 10B). As an example, a PMMA resist mask can be dissolved in acetone. A second graphene layer 1100 is then deposited onto first layer of graphene ribbons 600a (FIGS. 11A and 11B) and coated with lithography resist mask 1200 (FIGS. 12A and 12B). As before, resist mask 1200 is patterned on first layer of graphene ribbons 600a in the shape of resist mask ribbons 1200a, but here, the resist mask ribbons 1200a are patterned perpendicular to first layer of graphene ribbons 600a (FIGS. 13A and 13B). Also as before, an etching technique is then used to etch away the graphene that is not protected by resist mask ribbons 1200a (FIGS. 14A and 14B), and the resist mask ribbons 1200a are then removed (FIGS. 15A and 15B). The resulting structure is plasmon-enhanced coupler 106a having a graphene ribbon array 204 that consists of periodic, alternating one and two layer graphene regions along the length of ribbons 208, 208a, 208b, 208c and 208d. The periodic layer characteristic of the graphene ribbons allows for enhanced bandwidth plasmon adsorption in the sensing platform, making detection more *facile*.

Figure 16:
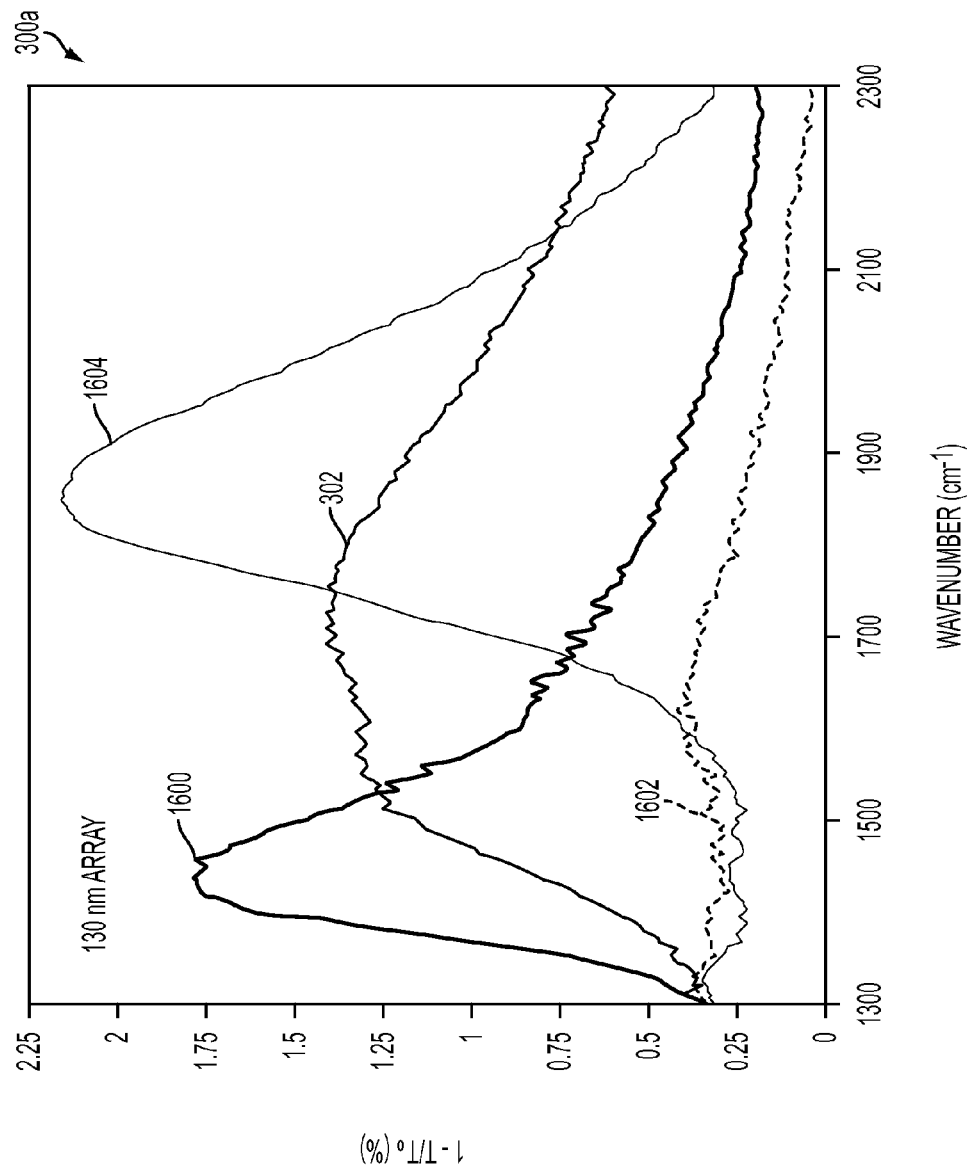
FIG. 16 depicts a graph illustrating evolution of the plasmon absorption during fabrication of the plasmon-enhanced coupler in accordance with one or more embodiments.

FIG. 16 is a graph 300a, similar to graph 300 shown in FIG. 3. Graph 300a also includes enhanced plasmon absorption 302 of the nanoribbon design shown in FIGS. 2A-2C. In addition, graph 300a also shows the evolution of the plasmon absorption during fabrication of the periodic layered nanoribbon array structure as shown in FIGS. 6B to 15b. Plasmon absorption 1600 represents the plasmon absorption of first graphene layer ribbons 600a of FIGS.

10A and 10B. Plasmon absorption 1602 represents the plasmon absorption of second graphene layer 1100 over first graphene layer ribbons 600a of FIGS. 11A and 11B. Plasmon absorption 1604 represents the plasmon absorption of a double-layer nanoribbon array for reference purposes. As shown, the bandwidth of enhanced plasmon absorption 302 is relatively wide, extending from about 1500 cm$^{-1}$ to about 2000 cm$^{-1}$ where the absorption percentage (shown along the vertical y axis) is above approximately 1. Also the bandwidth of enhanced plasmon absorption 302 is significantly wider than plasmon absorptions 1602, 1604 and 1606. Thus, as previously described, the broadened bandwidth of plasmon absorption 302 near the resonant peak allows for a wider range of frequencies to be probed, makes it easier to match coupler frequency with molecules of interest, and relaxes other design parameters that would otherwise need to be more tightly controlled in order to achieve frequency matching in the absence of plasmon-enhanced bandwidth provided by the present disclosure.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A plasmon-enhanced coupler, comprising:
   a first plasmon region having at least one first resonance peak frequency and at least one first resonance frequency bandwidth; and
   a second plasmon region having at least one second resonance frequency peak and at least one second resonance bandwidth;
   wherein a resonance frequency bandwidth of the plasmon-enhanced coupler is broader than either the at least one first resonance frequency bandwidth or the at least one second resonance frequency bandwidth;
   wherein a resonance peak frequency of the plasmon-enhanced coupler is between the at least one first resonance peak frequency and the at least one second resonance peak frequency.

2. The coupler of claim 1 wherein:
   said first plasmon region is sufficiently close to said second plasmon region to cause said at least one first resonance frequency to interact with said at least one second resonance frequency, thereby resulting in the resonance frequency bandwidth and the resonance peak frequency.

3. The coupler of claim 2 wherein:
   said resonance frequency bandwidth is chosen to overlap a frequency of interest; and
   radiation directed to the plasmon-enhanced coupler that is within said resonance frequency bandwidth is attenuated.

4. The coupler of claim 2 wherein:
   said first plasmon region comprises a first predetermined number of layers of conductive material; and
   said second plasmon region comprises a second predetermined number of layers of conductive material;
   wherein said first predetermined number is not equal to said second predetermined number.

5. The coupler of claim 4 wherein:
   said resonance frequency bandwidth is chosen to overlap a frequency of interest;
   said frequency of interest comprises a vibration frequency of certain molecules of interest; and
   radiation directed to the plasmon-enhanced coupler causes the plasmon-enhanced coupler to interact with said molecules of interest to result in alteration of said radiation.

6. The coupler of claim 5 wherein said alteration of said radiation comprises modulation of said radiation.

7. The coupler of claim 6 wherein said modulation is evaluated to derive information about said molecules of interest.

8. The coupler of claim 4 wherein:
   said first predetermined number of layers of conductive material comprise graphene; and
   said second predetermined number of layers of conductive material comprise graphene.

9. A system for detecting a plasmon resonance of a coupler, comprising:
   a coupler configured to receive light from a light;
   the coupler comprising a first plasmon; and
   the coupler further comprising a second plasmon;
   wherein the first plasmon region comprises a first predetermined number of layers of conductive material;
   wherein the second plasmon region comprises a second predetermined number of layers of conductive material;
   wherein the first predetermined number is not equal to said second predetermined number.

10. The system of claim 9 further comprising:
    a detector that converts light received from the coupler to an electrical signal; and
    an analyzer that analyzes said electrical signal to thereby analyze the plasmon resonance of the coupler.

11. The system of claim 10 wherein:
    said resonance frequency bandwidth is chosen to overlap a frequency of interest;

said frequency of interest comprises a vibration frequency of certain molecules of interest; and radiation directed to the plasmon-enhanced coupler causes the plasmon-enhanced coupler to interact with said molecules of interest to result in alteration of said radiation.

12. The system of claim 11 wherein said alteration of said radiation comprises modulation of said radiation.

13. The system of claim 12 wherein said analyzer evaluates said modulation to derive information about said molecules of interest.

14. A method of forming a plasmon-enhanced coupler, the method comprising:
forming a first plasmon region; and
forming a second plasmon region;
wherein said forming a first plasmon region and said forming a second plasmon region comprise:
forming a plurality of sections of a conductive material, each of said plurality of sections spaced from the other; and
forming over said plurality of sections at least one layer of conductive material;
wherein:
said first plasmon region comprises portions of said at least one layer of conductive material that are over said plurality of sections of conductive material; and
said second plasmon region comprises portions said at least one layer of conductive material that are not over said plurality of sections of conductive material.

15. The method of claim 14 wherein:
the first plasmon region includes at least one first resonance peak frequency and at least one first resonance frequency bandwidth; and
the second plasmon region includes at least one second resonance peak frequency and at least one second resonance frequency bandwidth;

a resonance frequency bandwidth of the plasmon-enhanced coupler is broader than either the at least one first resonance frequency bandwidth or the at least one second resonance frequency bandwidth;

a resonance peak frequency of the plasmon-enhanced coupler is between the at least one first resonance peak frequency and the at least one second resonance peak frequency; and the first plasmon region and the second plasmon region are sufficiently close that said at least one first resonance frequency interacts with said at least one second resonance frequency, thereby resulting in the resonance frequency bandwidth and the peak resonance frequency.

16. The method of claim 14 wherein:
said plurality of sections of conductive material comprise graphene; and
said at least one layer of conductive material comprises graphene.

17. The method of claim 15 wherein:
said resonance frequency bandwidth is chosen to overlap a frequency of interest;
said frequency of interest comprises a vibration frequency of certain molecules of interest; and
radiation directed to the plasmon-enhanced coupler causes the plasmon-enhanced coupler to interact with said molecules of interest to result in alteration of said radiation.

18. The method of claim 17 wherein said alteration of said radiation comprises modulation of said radiation.

19. The method of claim 18 wherein said modulation is evaluated to derive information about said molecules of interest.

* * * * *